United States Patent [19]

Smith et al.

[11] Patent Number: 5,130,488
[45] Date of Patent: Jul. 14, 1992

[54] PROCESS FOR PREPARING TERT-AMINE OXIDES

[75] Inventors: Kim R. Smith; James E. Borland, both of Baton Rouge, La.

[73] Assignee: Ethyl Corporation, Richmond, Va.

[21] Appl. No.: 591,426

[22] Filed: Oct. 1, 1990

Related U.S. Application Data

[63] Continuation-in-part of Ser. No. 415,910, Oct. 2, 1989, abandoned, which is a continuation-in-part of Ser. No. 344,275, Apr. 28, 1989, abandoned.

[51] Int. Cl.$^5$ .............................................. C07C 291/00
[52] U.S. Cl. ...................................... 564/298; 564/297
[58] Field of Search .............................. 564/297, 298

[56] References Cited

U.S. PATENT DOCUMENTS

| | | | |
|---|---|---|---|
| 3,275,673 | 9/1966 | Barlow | 564/298 |
| 3,776,959 | 12/1973 | Stalioraitis et al. | 564/298 |
| 4,247,480 | 1/1981 | Murata et al. | 564/298 |
| 4,659,565 | 4/1987 | Smith et al. | 564/298 |
| 4,748,275 | 5/1988 | Smith et al. | 564/298 |
| 4,942,260 | 7/1990 | Laurenzo et al. | 564/298 |

FOREIGN PATENT DOCUMENTS

| | | | |
|---|---|---|---|
| 1080112 | 4/1960 | Fed. Rep. of Germany | 564/297 |
| 2632638 | 12/1989 | France | 564/298 |

OTHER PUBLICATIONS

Ruppert, W., "Amine Oxides", CA 55, 17501 i, 1961.
Ochiai, E., *Aromatic Amine Oxides*, Chap. 2, sec. 2.1.1, pp. 6–7, 1967.

*Primary Examiner*—Glennon H. Hollrah
*Assistant Examiner*—Peter G. O'Sullivan
*Attorney, Agent, or Firm*—Patricia J. Hogan

[57] ABSTRACT

Discrete tert-amine oxides, including non-hygroscopic tert-amine oxide dihydrates, are prepared by (A) reacting a concentrated aqueous hydrogen peroxide with a tert-amine corresponding to the formula RR'R"N in which R is a primary alkyl group containing 8–24 carbons; R' is methyl, ethyl, or 2-hydroxyethyl; and R" is independently selected from methyl, ethyl, 2-hydroxyethyl, and primary alkyl groups containing 8–24 carbons in a reaction mixture which is maintained stirrable throughout the reaction by the use, at least during the latter part of the reaction, of an organic solvent which solubilizes the reaction mixture at the reaction temperature but permits precipitation of the tert-amine oxide at a lower temperature and (B) adjusting the water content of the product, if necessary, to achieve a water/tert-amine oxide mol ratio not higher than about 2.1/1 before recovering the tert-amine oxide.

19 Claims, No Drawings

PROCESS FOR PREPARING TERT-AMINE OXIDES

CROSS-REFERENCE TO RELATED APPLICATIONS

This application is a continuation-in-part of copending application Ser. No. 415,910, filed Oct. 2, 1989, now abandoned which in turn is a continuation-in-part of Ser. No. 344,275, filed Apr. 26, 1989 now abandoned.

FIELD OF INVENTION

The invention relates to a process for preparing solid tert-amine oxides from mixed tert-amines in which the organic groups attached to the nitrogen include at least one long-chain group and at least one short chain group.

BACKGROUND

As taught in U.S. Pat. No. 4,748,275 (Smith et al.) and the references discussed therein, there are many known methods of reacting mixed tert-amines with aqueous hydrogen peroxide to form tert-amine oxides including at least one long-chain group and at least one short-chain group.

The syntheses most commonly employed for the preparation of these oxides are the aqueous processes utilizing sufficient water to provide the products as aqueous solutions, including the processes of U.S. Pat. No. 4,247,480 (Murata et al.) in which carbon dioxide is used to promote the reaction. The aqueous processes are quite satisfactory for the products which are to be used in applications in which their water content can be tolerated. However, the utilization of these processes necessitates the performance of after-treatments, such as spray-drying or evaporation, when the amine oxides are intended for use in applications, such as dry solid laundry detergent formulations, in which the presence of the solvent cannot be tolerated.

Less commonly, the tert-amine oxides are prepared in organic solvents, as in U.S. Pat. No. 3,776,959 (Stalioraitis et al.). These processes are also very satisfactory for some purposes, but their being designed to form the amine oxides in solution makes them present the same type of problem as the aqueous processes when they are employed to prepare amine oxides that are intended for use in applications in which the presence of a solvent cannot be tolerated. After-treatments are required to remove the solvent.

Smith et al. teach that some tert-amine oxides can be prepared in the solid form that makes them more desirable than the dissolved oxides for some purposes. Their process uses temperatures high enough to maintain the product in a molten state.

Some tert-amine oxides have been synthesized as dihydrates; and German Auslegeschrift 1,080,112 (Ruppert) teaches that trimethylamine oxide dihydrate can be prepared by oxidizing trimethylamine with dilute hydrogen peroxide in the presence of ethyl formate as a catalyst at 30°-40° C., decomposing excess hydrogen peroxide, and concentrating the product solution by vacuum evaporation. However, the mixed tert-amine oxides including at least one long-chain group have not previously been prepared in dihydrate form. It is possible that it was not thought even possible to prepare such dihydrates because of the hygroscopicity that would have been expected to be imparted by the long-chain group or groups.

SUMMARY OF INVENTION

It has now been found that discrete tert-amine oxides, including non-hygroscopic dihydrates, can be prepared by oxidizing certain mixed tert-amines with aqueous hydrogen peroxides having a concentration of 50-90% by weight at 20°-100° C. in the presence, at least during the latter part of the reaction, of an organic solvent in which the tert-amine and tert-amine oxide are soluble at the reaction temperature but in which the tert-amine oxide is insoluble at a lower temperature when (1) the amount of solvent used is sufficient to maintain the reaction mixture fluid and stirrable throughout the reaction and (2) the water content of the product, if not inherently such as to provide a water/tert-amine oxide mol ratio not higher than about 2.1/1 because of the amount of aqueous hydrogen peroxide used, is adjusted to achieve such a ratio before the tert-amine oxide is recovered.

The mixed tert-amines that can be oxidized in this process are compounds corresponding to the formula RR'R"N in which R is a primary alkyl group containing 8-24 carbons; R' is methyl, ethyl, or 2-hydroxyethyl; and R" is independently selected from methyl, ethyl, 2-hydroxyethyl, and primary alkyl groups containing 8-24 carbons.

DETAILED DESCRIPTION

As just indicated, the tert-amines that can be used in the practice of the invention are those which contain one or two short-chain groups independently selected from methyl, ethyl, and 2-hydroxyethyl groups, with the remaining valence or valences of the amino nitrogen being satisfied with long-chain groups independently selected from primary alkyl groups containing 8-24 carbons, e.g., octyl, decyl, dodecyl, tetradecyl, hexadecyl, octadecyl, eicosyl, docosyl, and tetracosyl groups. The primary alkyl groups may be branched-chain groups, but the preferred amines are those in which at least most of the primary alkyl groups have a straight chain.

Exemplary of these tert-amines are N-octyldimethylamine, N,N-didecylmethylamine, N-decyl-N-dodecylethylamine, N-dodecyldimethylamine, N-tetradecyldimethylamine, N-tetradecyl-N-ethylmethylamine, N-tetradecyl-N-ethyl-2-hydroxyethylamine, N,N-ditetradecyl-2-hydroxyethylamine, N-hexadecyldimethylamine, N-hexadecyldi-2-hydroxyethylamine, N-octadecyldimethylamine, N,N-dieicosylethylamine, N-docosyl-N-2-hydroxyethylmethylamine, N-tetracosyldimethylamine, etc.

The aqueous hydrogen peroxide employed in the reaction may be any aqueous hydrogen peroxide having a concentration of 50-90% by weight. However, to avoid the necessity of having to adjust the water content of the product at the end of the reaction, it is generally preferred to use a hydrogen peroxide having a concentration such that, in the amount employed, it inherently provides a product having the desired water/tert-amine oxide mol ratio.

As is customary in oxidations of tert-amines, the amount of hydrogen peroxide incorporated into the reaction mixture is at least a stoichiometric amount and is generally about 1.1-1.3, preferably about 1.15-1.25 times the stoichiometric amount.

The organic solvent may be any organic liquid in which the tert-amine and tert-amine oxide are soluble at the reaction temperature but in which the tert-amine oxide is insoluble at a lower temperature. However, to avoid the danger of explosion, this solvent should be substantially inert; and, in a preferred embodiment of the invention, it is a solvent which is capable of maintaining the reaction mixture fluid and stirrable without being used in an amount that would reduce the solids content of the reaction mixture below 50% by weight.

Based on cost and availability, as well as effectiveness, the solvents apt to be desired for use in the process are the liquids which are esters, hydrocarbons, halohydrocarbons, or highly polar aprotic solvents, such as dimethylformamide, dimethylacetamide, diethylformamide, diethylacetamide, and mixtures thereof.

The solvents that are generally preferred are the ester solvents. Suitable esters include saturated and unsaturated aliphatic, cycloaliphatic, and aromatic esters such as methyl formate, ethyl acetate, 1-butenyl formate, 2-isobutenyl propionate, cyclohexyl hexanoate, phenyl acetate, phenethyl propionate, ethyl 2-methylbenzoate, butyl 4-butoxybenzoate, ethylene glycol diacetate, glycerol monooleate, glycerol monostearate, glycerol distearate, glycerol tributyrate, glucose dibutyrate, etc. However, the preferred esters are the alkyl alkanoates, especially those in which the alkyl groups contain 1-5 carbons and the alkanoic moieties contain 2-5 carbons.

Exemplary of the preferred ester solvents are methyl acetate, ethyl acetate, isopropyl acetate, butyl acetate, secbutyl acetate, t-butyl acetate, isobutyl acetate, amyl acetate, and the corresponding propionates, butyrates, and valerates.

When the solvent is a hydrocarbon, it is generally a liquid aliphatic, cycloaliphatic, or aromatic hydrocarbon such as hexane, isohexane, heptane, 2-ethylhexane, octane, isooctane, cyclohexane, cyclooctane, toluene, or the like, which may contain up to about 10% (e.g., 2-10%) by weight of a polar co-solvent, such as isopropanol or other alcohol, to increase the size of the amine oxide crystals that precipitate from the solvent. The use of a non-polar solvent alone leads to the precipitation of very fine gel-like crystals which take longer to recover by filtration.

Halohydrocarbons that are apt to be found particularly useful in the reaction are aromatic halohydrocarbons such as chlorobenzene, dichlorobenzene, bromobenzene, chlorotoluene, 2,4-dichlorotoluene, and the like.

The process of the invention is conducted by adding the aqueous hydrogen peroxide to the amine, preferably at a controlled rate and preferably in the presence of carbon dioxide and/or a chelating agent, such as diethylenetriaminepentaacetic acid or ethylenediaminetetraacetic acid, at a temperature of about 20°-100° C., preferably about 25°-80° C., and maintaining the reaction temperature until the oxidation is substantially complete in about 1-24 hours. When carbon dioxide is added to promote the reaction, the entire reaction can be conducted at the lower temperatures, e.g., 20°-40° C. However, even when carbon dioxide is used, it is generally preferred to conduct at least the latter part of the reaction at the higher temperatures, e.g., 60°-80° C., to speed the reaction.

The organic solvent may be present throughout the reaction. However, it is generally preferred to insure minimization of the amount of solvent used by initiating the reaction in the absence of the solvent or any other medium except the water contributed by the aqueous hydrogen peroxide and then gradually adding the solvent during the course of the reaction only as needed to maintain the reaction mixture fluid and stirrable.

When the reaction has been completed, the amine oxide may be recovered immediately if the hydrogen peroxide has been used in an amount and concentration such as to form a product having the desired water/tert-amine oxide mol ratio not higher than about 2.1/1, the particular mol ratio desired varying with the form in which it is wished to recover the amine oxide. The oxide is recovered in dihydrate form when the product from which it is recovered has a water/tert-amine oxide mol ratio in the range of about 1.9-2.1/1. When the product has a lower water/tert-amine oxide mol ratio, the recovered oxide is less than 100% dihydrate. For example, it is a mixture of the dihydrate, the monohydrate, and anhydrous tert-amine oxide when the water/tert-amine oxide mol ratio is about 0.9-1.1/1.

Adjustment of the water/tert-amine oxide mol ratio in the product, when necessary, is accomplished by adding the appropriate amount of water to the product or by removing the excess water. When it is necessary to remove water, the removal may be effected by azeotropic distillation, with additional solvent being added during the distillation or the removed solvent being returned by the use of a Dean-Stark trap to prevent gelation of the product.

The tert-amine oxide may be recovered by distilling off the organic solvent, if desired. However, it is preferred to recover the amine oxide by taking advantage of the nature of the organic solvent and simply cooling the product to a temperature at which the amine oxide is no longer soluble in the solvent, allowing the oxide to precipitate, and separating the precipitate by filtration. When this preferred recovery technique is used, it is generally most preferred to dilute the product with additional organic solvent before precipitation is allowed to occur.

The purity of the amine oxide may be improved by recrystallizing it one or more times from the same organic solvent in which it was prepared or from a different organic solvent in which it can be dissolved at a higher temperature and from which it can be precipitated at a lower temperature.

This recrystallization technique can also be used to reduce the water content of the recovered amine oxide, if desired, by using an organic solvent, such as ethyl acetate, in which water is at least partially soluble. For example, if the amine oxide is recovered as a dihydrate, and it is wished to convert it to an oxide containing a lesser amount of water, e.g., to a mixture of dihydrate, monohydrate, and anhydrous oxide or to the monohydrate or anhydrous form, the amine oxide can be recrystallized from such an organic solvent until the desired degree of dehydration is accomplished.

The invention is advantageous as a means of preparing mixed tert-amine oxides that can be used in the preparation of powdered compositions, such as dry laundry detergent formulations, without first being subjected to after-treatments that could increase their cost and/or contaminate them with materials used in the after-treatments or decomposition products formed during the after-treatments.

The amine oxides formed by the process can all be regarded as solids, although the lower molecular weight ones have melting points that put them at the borderline between solids and liquids at some use temperatures; and the amine oxides that are recovered as dihydrates have the additional advantage of being nonhygroscopic. These products, whether they are dihydrates, amine oxides which are less than 100% dihydrate, monohydrates, or anhydrous amine oxides, have general utility in the same applications as the mixed tert-amine oxides prepared by conventional techniques, although their primary attractiveness is their having a form that makes them so well suited for incorporation into dry formulations.

The following examples are given to illustrate the invention and are not intended as a limitation thereof.

EXAMPLE I

Charge a suitable reaction vessel with 100 g (0.41 mol) of N-tetradecyldimethylamine and 0.5 g (1.27 mmols) of diethylenetriaminepentaacetic acid. Heat the mixture with stirring to 65° C., add 23 g (0.47 mol) of 70% aqueous hydrogen peroxide dropwise over a 15-minute period, then raise the temperature to 75°–76° C., and stir at that temperature for seven hours while adding 34 mL of ethyl acetate dropwise as needed to maintain a clear, gel-free liquid. NMR analysis shows 99% conversion of the amine. Recover the product by adding the crude reaction mass to 400 mL of ethyl acetate and cooling to 15° C. to precipitate nonhygroscopic white crystals, which analysis shows to be N-tetradecyldimethylamine oxide dihydrate, a solid having a melting point of about 41' C. The recovered yield is 86%.

COMPARATIVE EXAMPLE

Repeat Example I except for employing no ethyl acetate. After 15 minutes at 75°–76° C., the reaction mixture forms a paste which cannot be fluidized even by increasing the temperature and holding it at 95° C. for 24 hours. Analysis of the crude reaction mass at that time shows 94% amine conversion.

EXAMPLE II

Repeat Example I except for continuing the reaction for an additional hour to exceed 99% conversion and recovering the product by vacuum-stripping the ethyl acetate from the crude reaction mass. The recovered yield of solid N-tetradecyldimethylamine oxide dihydrate is about 98%.

EXAMPLE III

Repeat Example I except for using 35 g (0.51 mol) of 50% aqueous hydrogen peroxide, increasing the total amount of ethyl acetate added during the reaction to 54 mL, and continuing the reaction for an additional hour. NMR analysis shows 85% amine conversion. Dilute the reaction mass with 65 mL of ethyl acetate, azeotrope about 16 mL of water from the mass, pour the remaining material into 400 mL of ethyl acetate, and hold the solution overnight in a 15° C. water bath to crystallize the product. Filtration then provides a 43% recovered yield of crystalline N-tetradecyldimethylamine oxide dihydrate.

EXAMPLE IV

Repeat Example I except for substituting methyl propionate for the ethyl acetate and adding a total of 37 mL of the solvent during the reaction. NMR analysis shows 99% amine conversion. Dissolve the crude reaction mass in 300 mL of methyl propionate and cool to 10° C. to crystallize N-tetradecyldimethylamine oxide dihydrate in a 48% yield.

EXAMPLE V

Repeat Example I except for substituting butyl acetate for the ethyl acetate and adding a total of 40 mL of the solvent during the reaction. NMR analysis shows 99% amine conversion. Dissolve the crude reaction mass in 300 mL of butyl acetate and cool the solution to 15° C. to crystallize N-tetradecyldimethylamine oxide dihydrate in an 85% yield.

EXAMPLE VI

Repeat Example I except for substituting sec-butyl acetate for the ethyl acetate and adding a total of 50 mL of the solvent during the reaction. NMR analysis shows 99% amine conversion. Dissolve the crude reaction mass in 300 mL of sec-butyl acetate and cool the solution to 15° C. to crystallize N-tetradecyldimethylamine oxide dihydrate in a 74% yield.

EXAMPLE VII

Repeat Example I except for substituting methyl benzoate for the ethyl acetate and adding a total of 40 mL of the solvent during the reaction. NMR analysis shows 99% amine conversion. Dissolve the crude reaction mass in 300 mL of methyl benzoate and cool the solution to 15° C. to crystallize N-tetradecyldimethylamine oxide dihydrate in a 79% yield.

EXAMPLE VIII

Charge a suitable reaction vessel with 100 g (0.32 mol) of N,N-didecylmethylamine and 0.5 g (1.27 mmols) of diethylenetriaminepentaacetic acid. Heat the reaction mixture with stirring to 65° C., add 18 g (0.37 mol) of 70% aqueous hydrogen peroxide dropwise over a 15-minute period, then raise the temperature to 75°–76° C., and stir at that temperature for four hours while adding 10 mL of ethyl acetate dropwise as needed to maintain a clear, homogeneous liquid. NMR analysis shows 99% amine conversion. Dissolve the crude reaction mass in 400 mL of ethyl acetate and cool to 5° C. to precipitate non-hygroscopic white crystals, which analysis shows to be N,N-didecylmethylamine oxide dihydrate, a solid having a melting point of about 104.C. The recovered yield is 34%.

EXAMPLE IX

Charge a suitable reaction vessel with 100 g (0.41 mol) of N-tetradecyldimethylamine and 0.5 g (1.27 mmols) of diethylenetriaminepentaacetic acid. Stir the mixture at 65° C. under a carbon dioxide atmosphere while making dropwise additions of 24 g (0.49 mol) of 70% aqueous hydrogen peroxide and 28 mL of ethyl acetate over a 10-minute period. The stir the reaction mixture at 75° C. for two hours, continuing the dropwise addition of the ethyl acetate during the first 19 minutes to keep the reaction mixture clear and gel-free and provide a total of 43 mL of ethyl acetate therein. NMR analysis shows 100% amine conversion. Dissolve the crude reaction mass in 500 mL of ethyl acetate and cool to 15° C. to crystallize N-tetradecyldimethylamine oxide dihydrate in an 87% yield.

EXAMPLE X

Repeat Example IX except for using only 23 g of the aqueous hydrogen peroxide, employing N,N-dimethylacetamide as the solvent, and adding the hydrogen peroxide and the first portion of the solvent over a period of five minutes. The total amount of solvent added during and after the hydrogen peroxide addition is 45 mL. Pour the resultant reaction mixture into 200 mL of N,N-dimethylacetamide and cool to 10° C. to precipitate crystalline N-tetradecyldimethyl amine oxide dihydrate.

EXAMPLE XI

Repeat Example X except for using toluene as the solvent. The N-tetradecyldimethylamine oxide dihydrate precipitate is gel-like.

EXAMPLE XII

Repeat Example XI except for including 5% by weight of isopropanol in the toluene solvent. The N-tetradecyldimethylamine oxide dihydrate precipitate is crystalline.

EXAMPLE XIII

Repeat Example X on a smaller scale except for using heptane as the solvent, the total volume of heptane required to keep the reaction mixture fluid being about 10 times the volume of N,N-dimethylacetamide required on the same scale. The N-tetradecyldimethylamine oxide dihydrate precipitates as fine crystals.

What is claimed is:

1. A process which comprises (A) preparing a tert-amine oxide by reacting (1) a mixed tert-amine corresponding to the formula RR'R''N in which R is a primary alky group containing 8–24 carbons; R' is methyl, ethyl, or 2-hydroxyethyl; and R'' is independently selected from methyl, ethyl, 2-hydroxyethyl, and primary alkyl groups containing 8–24 carbons with (2) at least a stoichiometric amount of an aqueous hydrogen peroxide having a concentration of 50–90% by weight at a temperature in the range of 20°–100° C., at least the latter part of the reaction being conducted in an organic solvent in which the tert-amine and tert-amine oxide are soluble at the reaction temperature but in which the tert-amine oxide is insoluble at a lower temperature; the amount of solvent being sufficient to maintain the reaction mixture fluid and stirrable throughout the reaction, (B) adjusting the water content of the product, if necessary, to achieve a water/tert-amine oxide mol ratio not higher than about 2.1/1, and (C) recovering the tert-amine oxide by cooling a solution of the oxide in the organic solvent until the oxide precipitates.

2. The process of claim 1 wherein the mixed tert-amine is one in which R and R'' are independently selected from primary alkyl groups containing 8–24 carbons.

3. The process of claim 1 wherein the mixed tert-amine is one in which R' and R'' are independently selected from methyl, ethyl, and 2-hydroxyethyl groups.

4. The process of claim 1 wherein the amount and concentration of the aqueous hydrogen peroxide are such as to provide the desired water/tert-amine oxide mol ratio not higher than about 2.1/1 without any adjustment of the water content of the product.

5. The process of claim 1 wherein the reaction temperature is in the range of 25°–80° C.

6. The process of claim 1 conducted in the presence of added carbon dioxide.

7. The process of claim 1 wherein the organic solvent is a liquid selected from the group consisting of esters, hydrocarbons, halohydrocarbons, and highly polar aprotic solvents.

8. The process of claim 7 wherein the organic solvent is an ester.

9. The process of claim 8 wherein the ester is ethyl acetate.

10. The process of claim 7 wherein the organic solvent is an aromatic hydrocarbon which optionally contains up to 10% by weight of an alcohol as a co-solvent.

11. The process of claim 10 wherein the organic solvent is toluene containing 2–10% by weight of isopropanol as a cosolvent.

12. The process of claim 1 wherein the reaction is initiated in the absence of the organic solvent, which is gradually added during the course of the reaction only as needed to maintain the reaction mixture stirrable.

13. The process of claim 1 wherein the product from which the tert-amine oxide is recovered is one in which the water/tert-amine oxide mol ratio is about 1.9–2.1/1 so that the tert-amine oxide is recovered in the form of a tert-amine oxide dihydrate.

14. The process of claim 13 wherein the recovered tert-amine oxide dihydrate is recrystallized from a solvent capable of dissolving water until the oxide is in the form of a monohydrate.

15. The process of claim 13 wherein the recovered tert-amine oxide dihydrate is recrystallized from a solvent capable of dissolving water until the oxide is substantially anhydrous.

16. The process of claim 1 wherein the product from which the tert-amine oxide is recovered is one in which the water/tert-amine oxide mol ratio is about 0.9–1.1/1.

17. The process of claim 1 wherein the organic solvent employed in the process is supplemented with additional organic solvent before the solution is cooled.

18. The process of claim 17 wherein the precipitated tert-amine oxide is recrystallized one or more times to increase its purity.

19. The process of claim 1 wherein the mixed tert-amine is reacted with an amount of the aqueous hydrogen peroxide such as to provide the desired water/tert-amine oxide mol ratio not higher than about 2.1/1; the temperature is in the range of 25°–80° C.; the organic solvent is ethyl acetate, which is gradually added during the course of the reaction only as needed to maintain the reaction mixture stirrable; the tert-amine is recovered by diluting the product with additional ethyl acetate and cooling the resultant solution until the oxide precipitates; and the precipitated tert-amine oxide is recrystallized one or more times to increase its purity.

* * * * *